United States Patent
Chadi

(10) Patent No.: US 10,417,764 B2
(45) Date of Patent: Sep. 17, 2019

(54) SYSTEM AND METHODS FOR DIAGNOSTIC IMAGE ANALYSIS AND IMAGE QUALITY ASSESSMENT

(71) Applicant: EYES LTD, Bet Shemesh (IL)

(72) Inventor: Benjamin H. Chadi, Great Neck, NY (US)

(73) Assignee: EYES LTD, Bet Shemesh (IL)

( * ) Notice: Subject to any disclaimer, the term of this patent is extended or adjusted under 35 U.S.C. 154(b) by 0 days.

(21) Appl. No.: 16/089,004

(22) PCT Filed: Mar. 29, 2017

(86) PCT No.: PCT/IL2017/050391
§ 371 (c)(1),
(2) Date: Sep. 27, 2018

(87) PCT Pub. No.: WO2017/168424
PCT Pub. Date: Oct. 5, 2017

(65) Prior Publication Data
US 2019/0197683 A1    Jun. 27, 2019

Related U.S. Application Data

(60) Provisional application No. 62/315,715, filed on Mar. 31, 2016.

(51) Int. Cl.
*G06K 9/32* (2006.01)
*G06T 7/00* (2017.01)
(Continued)

(52) U.S. Cl.
CPC .......... *G06T 7/0012* (2013.01); *A61B 5/0044* (2013.01); *A61B 5/743* (2013.01);
(Continued)

(58) Field of Classification Search
CPC ................ G06T 7/0012; G06T 7/13; G06T 2207/30048; A61B 5/0044; A61B 5/743; G06K 9/3233
See application file for complete search history.

(56) References Cited

U.S. PATENT DOCUMENTS 7,043,080 B1    5/2006  Dolan
9,355,458 B2 *  5/2016  Ihara ..................... A61B 5/08
(Continued)

OTHER PUBLICATIONS

Khunteta et al., Edge Detection via Edge-Strength Estimation Using Fuzzy Reasoning and Optimal Threshold Selection Using Particle Swarm Optimization, Advances in Fuzzy Systems, Dec. 14, 2014, pp. 1-18.
(Continued)

*Primary Examiner* — Phuoc Tran
(74) *Attorney, Agent, or Firm* — The Roy Gross Law Firm, LLC; Roy Gross

(57) ABSTRACT

A method of analyzing and assessing an image comprises the steps of: (a) obtaining said image in a digital form; (b) processing said image; and (c) establishing at least one edge line within said image. The step of processing said image further includes: (a) building a 3D graph of intensity distribution within said image; (b) calculating identifying vector angle values (IVAVs); said angles adjoin to points of said 3D intensity distribution graph which correspond to individual pixels of said image; said angles lie in a plane defined by an intensity axis of said image; (c) setting a range of lower and upper thresh-hold level values (THLV1 and THLV2) between which edge points are indicatable; and (d) indicating edge points according to said THLV1 and THLV2.

20 Claims, 5 Drawing Sheets

(51) Int. Cl.
*A61B 5/00* (2006.01)
*G06T 7/13* (2017.01)

(52) U.S. Cl.
CPC .............. *G06K 9/3233* (2013.01); *G06T 7/13* (2017.01); *G06T 2207/30048* (2013.01)

(56) References Cited

U.S. PATENT DOCUMENTS

2007/0116342 A1* 5/2007 Zarkh ................... G06T 7/564
   382/130
2009/0279758 A1* 11/2009 Dikici ................... G06T 7/11
   382/128
2012/0026352 A1 2/2012 Natroshvili et al.

OTHER PUBLICATIONS

International Search Report of PCT/IL2017/050391 Completed Jul. 5, 2017; dated Jul. 9, 2017 3 Pages.
Witten Opinion of PCT/IL2017/050391 Completed Jul. 5, 2017; dated Jul. 9, 2017 5 Pages.
International Preliminary Report on Patentability of PCT/IL2017/050391 completed Mar. 11, 2018; dated Aug. 28, 2018 15 Pages.

* cited by examiner

SYSTEM AND METHODS FOR DIAGNOSTIC IMAGE ANALYSIS AND IMAGE QUALITY ASSESSMENT

RELATED APPLICATIONS

This application is a National Phase of PCT Patent Application No. PCT/IL2017/050391 having International filing date of Mar. 29, 2017, which claims the benefit of priority of U.S. Provisional Application No. 62/315,715 filed on Mar. 31, 2016. The contents of the above applications are all incorporated by reference as if fully set forth herein in their entirety.

FIELD OF THE INVENTION

The present invention relates generally to the field of image assessment and analysis. More specifically, the present invention relates to an automated image analysis and image quality assessment based on the extraction of predefined data from the input of images to be used for further analysis as accurate quantitative measurements and qualitative inferences regarding individuals and classes of objects in the image.

BACKGROUND OF THE INVENTION

The following description includes information that may be useful in understanding the present invention. It is not an admission that any of the information provided herein is prior art or relevant to the presently claimed invention, or that any publication specifically or implicitly referenced is prior art.

Scientific endeavors generally require precise and accurate quantification to determine results. In medicine and in the field of cardiology in particular, the results obtained from various tests are used in further decision-making regarding the patient including accurate diagnosis and treatment. Many tests, especially those involving imaging, provide results that require great skill to analyze by a trained expert or specialist. Due to the huge amount of information presented in an image and the lack of accurate fully automated systems for analysis, the field of medicine is frequently left to semi-quantitation (e.g., grade on a 1 to 4 scale). While this may be adequate for many purposes, observer bias, lack of reproducibility, and lack of the ability to be precise often results in the need for more testing to try to be certain of the diagnosis, or painstaking effort by the physician to make sure the treatment is given in the effective regions (e.g., that the proper location on the field of image is treated by X-rays, etc.). The ability to perform rapid and accurate quantification using computer-assisted image analysis can be a great aid in these fields.

Currently there have been great limitations in the full automation of image analysis. There are edge-detection system and methods available that look for a general change in the picture but generally require noise subtraction and input from a user to focus on the areas of interest or from an encyclopedic database to compare the image to in order to identify or delimit the object of interest in the image. The edges detected are generally based on first and second differentiation and are binary (edge present/absent) but not qualitative (do not reflect information about different types of edges present). Users of current processes need frequent and direct operator input to effectuate an analysis.

None of the current technologies and prior art, taken alone or in combination, address nor provide a utility solution for a fully automated precise image analysis and image quality assessment based on the extraction of predefined data from the input of images using a real-time simultaneous technology. The present invention can identify fine edges and distinguish between different objects without the need to make assumptions about the input image or to use filters or noise reduction methods that result in a net loss of data.

Specific uses and applications of this process include the field of coronary angiography and echocardiography. The raw images obtained in these arts including cineangiograms of the coronary arteries and echo images of the cardiac chamber walls until presently have not readily been amenable to accurate fully automated analysis of artery caliber (diameter along its length to evaluate amount of stenosis) or chamber dimensions and wall thickness.

In coronary angiography until present the cardiologist has had to estimate the percent stenosis along the length of the artery as revealed by the gold standard coronary angiogram (luminogram) or by other techniques including intravascular ultrasound or Computerized Tomographic (CT) scan. However, actual automation of this analysis is burdensome and currently has been inaccurate and therefore unreliable. Using the new detection methods inside a larger method of straightening the artery so that perpendicular cuts are obtained for measurement is providing the ability for both a fully automated and a more accurate analysis of the whole length of the artery.

In echocardiography field, there is currently no fully automated method of measuring cardiac chamber borders and dimensions. The input of the technologist is required in multiple steps of the image analysis. The new method is being developed to enable fully automated chamber measurements and wall thickness analyses and ejection fraction calculation. This would enable accurate noninvasive hemodynamic and cardiac output determinations.

Furthermore, great promise is expected in the field of artificial vision. By comparing two pictures temporally or side-by-side, with the fine resolution and discriminating abilities of the new method, the distances and dimensions of objects will be quickly amenable to calculation. By efficiently and automatically determining the shape and size of the object, automated identification should be greatly improved.

Further uses include the field of CT and MRI (magnetic resonance imaging) and ultrasound scans. The ability to accurately automatically measure chamber edges is expected to allow for automated analysis of normal and abnormal and for generation and comparison to encyclopedic database for further refinement of the art and science besides improving diagnosis and treatment for each individual patient. Another use would be for automated identification and marking of an organ edge for radiation therapy, for example.

US 20130278776 discloses a method for automatic left ventricular (LV) inner border detection. The method comprises the steps of: performing image mapping on an echocardiogram in order to produce a multi-level image map; converting the image map into a binary image by attributing pixels of one or more darker levels of the image map to the LV cavity and pixels of one or more lighter levels of the image map to the myocardium; applying a radial filter to contours of the myocardium in the binary image, to extract an approximate inner border of the LV; and performing shape modeling on the approximate inner border, to determine the LV inner border.

It should be emphasized that precision of shape modelling of edge lines in binary images strongly depends on a dynamic range of the original image. The narrow dynamic range results in lower precision of obtained edge line. Thus, there is a long-felt and unmet need to provide a method and a device that overcomes the problems associated with the prior art.

SUMMARY OF THE INVENTION

It is hence one object of the invention to disclose a method of analyzing and assessing an image. The aforesaid method comprises the steps of: (a) obtaining said image in a digital form; (b) processing said image; and (c) establishing at least one edge line within said image.

It is a core purpose of the invention to provide the step of processing said image comprising: a) building a 3D graph of intensity distribution within said image; (b) calculating identifying vector angle values (IVAVs); said angles adjoin to points of said 3D intensity distribution graph which correspond to individual pixels of said image; said angles lie in a plane defined by an intensity axis of said image; (c) setting a range of lower and upper thresh-hold level values (THLV1 and THLV2) between which edge line points are indicatable; and (d) tracing said edge points according to said THLV1 and THLV2.

Another object of the invention is to disclose the step of processing said image comprising a sub-step of finding a central area of ventricular cavity carried out automatically or manually.

A further object of the invention is to disclose the step of tracing said edge line performed in polar coordinates with an origin positioned in said central area of ventricular cavity.

A further object of the invention is to disclose the step of tracing said edge line comprising a sub-step of finding discontinuities indicated by a jump of said IVAV and removing found discontinuities by connecting the previously found fragments of said edge line adjacent to said discontinuities.

A further object of the invention is to disclose the step of tracing said edge line comprising a sub-step of forming borders of an object selected from the group consisting of: epicardium and ventricular endocardium, of the left or right heart in the image and any combination thereof.

A further object of the invention is to disclose the boundaries of objects in an image which is an image obtained from a vehicle camera usable for identification of surrounding obstacles.

A further object of the invention is to disclose a step of calculating of a characteristic selected from the group consisting of: a minimal wall thickness, an epicardial ventricular volume, an endocardial ventricular volume, difference therebetween, and any combination thereof.

A further object of the invention is to disclose the device for analyzing and assessing an image. The aforesaid device comprises: (a) a unit configured for digital input of said image; (b) a processor configured for analyzing and assessing said image; (c) an interface unit configured for controlling said device and displaying processed images and contiguous data.

It is another core purpose of the invention to provide the processor is further configured for: (a) building a 3D graph of intensity distribution within said image; (b) calculating identifying vector angle values (IVAVs); said angles adjoin to points of said 3D intensity distribution graph which correspond to individual pixels of said image; said angles lie in a plane defined by an intensity axis of said image; (c) setting a range of lower and upper thresh-hold level values (THLV1 and THLV2) between which edge points are indi-catable; and (d) tracing said edge points according to said THLV1 and THLV2. A further object of the invention is to disclose a non-transitory computer-readable medium having thereon software instructions configured to cause a processor to perform operations comprising: (a) obtaining said image in a digital form; (b) establishing at least one edge line within said image.

It is another core purpose of the invention to provide the operation of processing said image comprising: (a) building a 3D graph of intensity distribution within said image; (b) calculating identifying vector angle values (IVAVs); said angles adjoin to points of said 3D intensity distribution graph which correspond to individual pixels of said image; said angles lie in a plane defined by an intensity axis of said image; (c) setting a range of lower and upper thresh-hold level values (THLV1 and THLV2) between which edge points are indicatable; and (d) tracing said edge points according to said THLV1 and THLV2.

BRIEF DESCRIPTION OF THE PREFERRED EMBODIMENTS

The novel features believed to be characteristics of the invention are set the appended claims. The invention itself, however, as well as the preferred mode of use, further objects and advantages thereof, will best be understood by reference to the following detailed description of illustrative embodiment when read in conjunction with the accompanying drawings, wherein:

DETAILED DESCRIPTION OF THE PREFERRED EMBODIMENTS

The following description is provided, so as to enable any person skilled in the art to make use of said invention and sets forth the best modes contemplated by the inventor of carrying out this invention. Various modifications, however, are adapted to remain apparent to those skilled in the art, since the generic principles of the present invention have been defined specifically to provide method, device and software for analyzing and assessing an image.

The term "intensity" refers hereinafter to an intensity value of a gray scale image, an integral intensity value of a color image, an intensity value of a color selected image and combination thereof.

The term "image" refers hereinafter to any image in a digital form describable by a function of intensity distribution which includes recognizable edge structures. For example, the present invention is applicable to images captured by medical devices, surveillance cameras and alike.

Figure 1:
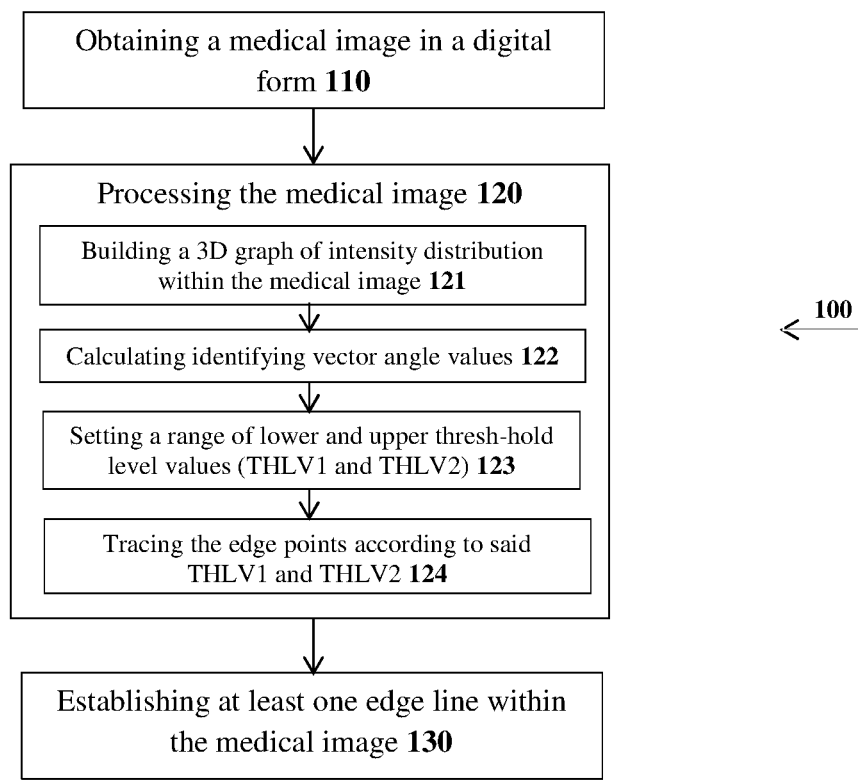
FIG. 1 is a flowchart of a method of analyzing and assessing an image.

Reference is now made to FIG. 1 presenting a flow chart of a method 100 of for analyzing and assessing an image. The known procedure includes providing the image to be analyzed and assessed in a digital form (step 110), processing the provided images (step 120) and establishing at least one edge line (step 130). In order to increase precision of pinpointing the edge line, step 120 comprises building a 3D graph of intensity distribution within the image (step 121). Then, at step 122, identifying vector angle values (IVAV) are calculated. The aforesaid angles adjoin to points of 3D intensity distribution graph which correspond to individual pixels of the image. The angles to be calculated lie in a vertical plane defined by an intensity axis (ordinate axis). Any function of original intensity function, such as its integral or differential, or a linear or quadratic modification, or combination of these, or other modifications or curves derived from the original intensity function used for obtaining the IVAVs are in the scope of the present invention.

At step 123, criteria of indicating an edge line are set. Specifically, lower and upper thresh-hold level values (THLV1 and THLV2) define an angle range in which the edge line is indicatable. When the THLV1 and THLV2 are applied to the calculated IVAVs, points meeting THLV1 and THLV2 requirements are traced (step 124). Thus, the obtained points form the sought-for edge line. IVAV and THLV expressed by means of any function of the aforesaid angles such as its complement, supplement, or its sine or cosine or tangent are in the scope of the present invention.

Figure 2A:
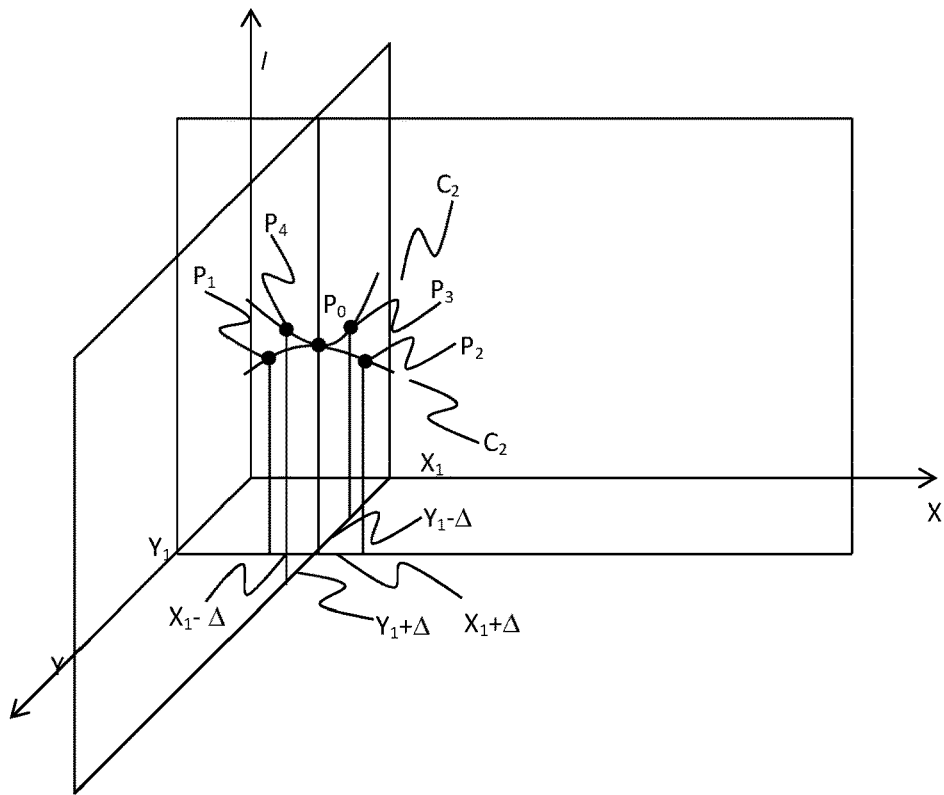
FIGS. 2a to 2e are schematic diagram explaining a procedure of scanning an image in polar coordinates and calculation of identifying vector angle values.

Reference is now made to FIG. 2a explaining the above-mentioned procedure. The 3D graph of intensity distribution within the image (not shown) is placed into Cartesian coordinates (I, X, Y). Planes $X=X_1$ and $Y=Y_1$ orthogonal to each other illustrate the process of scanning the 3D graph of intensity distribution in the polar coordinates. For each intensity curve $C_1/C_2$ lying in planes $X=X_1$ and $Y=Y_1$, IVAVs are calculated. Points $P_0$ to $P_4$ are the points on the 3D graph of intensity distribution and correspond to the pixels of the image to be analyzed. Point $P_0$ belongs curves $C_1$ and $C_2$ lying to both $X=X_1$ and $Y=Y_1$. Points $P_1$ and $P_2$ belong to $C_1$ lying in plane $X=X_1$ while $P_3$ and $P_4$ belong to $C_2$ lying in plane $Y=Y_1$.

Figure 2B:
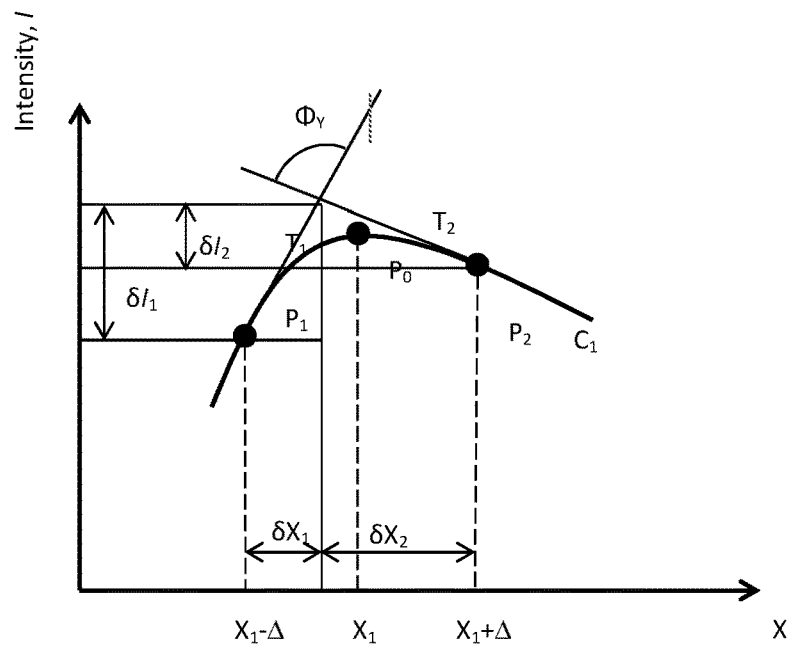
Figure 2C:
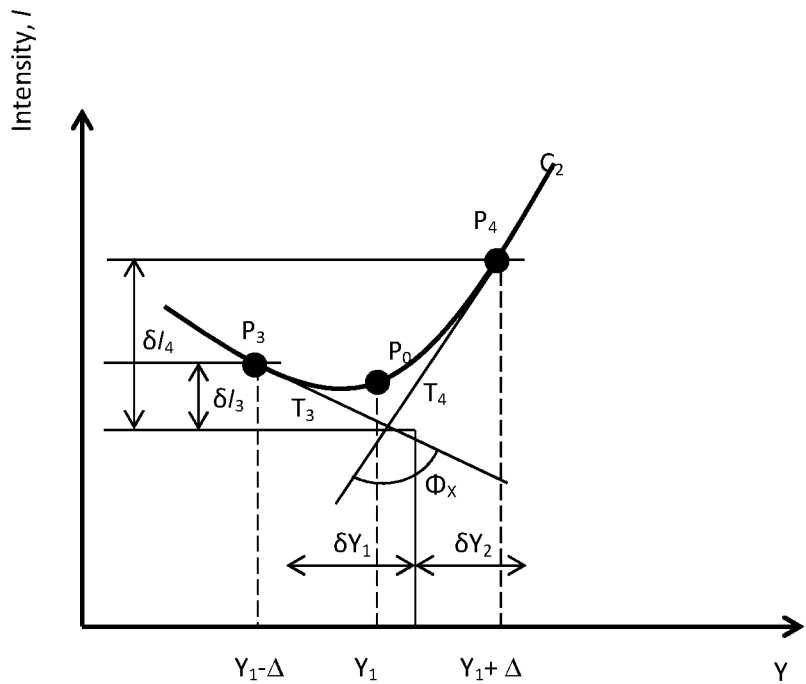

Reference is now made to FIGS. 2b and 2c illustrating calculation of an IVAV which is attributed to point $P_0$.

As seen in FIG. 2a, an Y-component of the IVAV of point $P_0$ $\Phi_Y$ is defined as a reciprocal between slopes of tangent lines $T_1$ and $T_2$ established in points $P_1$ and $P_2$ of curve $C_1$ corresponding to adjoining pixels.

Solving right triangles with respect to the rule of angle signs, we have for the Y-component:

$\varphi_Y = \text{atan}(\delta X_1/\delta I_1) - \text{atan}(\delta X_2/\delta I_2)$.

Referring to FIG. 2b, we have for the X-component:

$\Phi_X = \text{atan}(\delta Y_1/\delta I_3) - \text{atan}(\delta Y_2/\delta I_4)$.

Figure 2D:
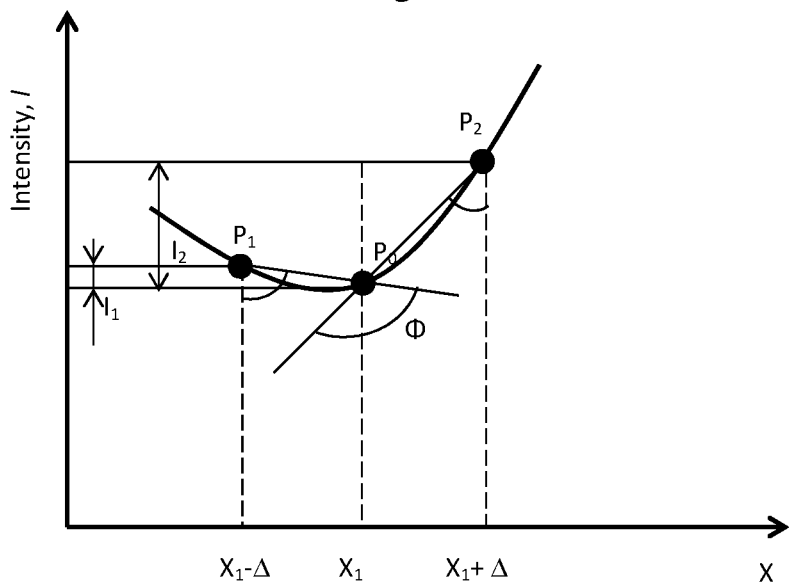

Reference is now made to FIG. 2d presenting a simplified approach to calculation of IVAVs. Specifically, the tangent lines are replaced with the lines interconnecting point $P_0$ with points $P_1$ and $P_2$. As defined above, the IVAV attributed to $P_0$, is a difference between the arccotangent of the slopes of the intensity curve in points $P_1$ and $P_2$, in this case, between arccotangent of the slopes of line segments $P_0P_1$ and $P_0P_2$.

The standard calculations give sought-for value $\Phi$:

$$\Phi = \mp \arcsin \frac{\Delta(I_1 - I_2)}{\sqrt{(\Delta^2 + I_1^2)(\Delta^2 + I_2^2)}}.$$

If calculated angle $\Phi_X$ or $\Phi_Y$ falls within the predetermined angle range between THLV1 and THLV2, pixel $P_0$ is indicated as an edge pixel. A greater number of components of angle $\Phi$ than 2 is also in the scope of the present invention. Pixels meeting the aforesaid criterion form the edge line. According to one embodiment of the present invention, a certain type of edge is indicated in the specific pixel location in the picture if either component $\Phi_X$ or $\Phi_Y$ falls between 0° and 15°.

According to an exemplary embodiment of the present invention, method, device and software for analyzing and assessing medical images is disclosed. All considerations in the present application concerning the left ventricle are equally applicable to the right ventricle.

Figure 2E:
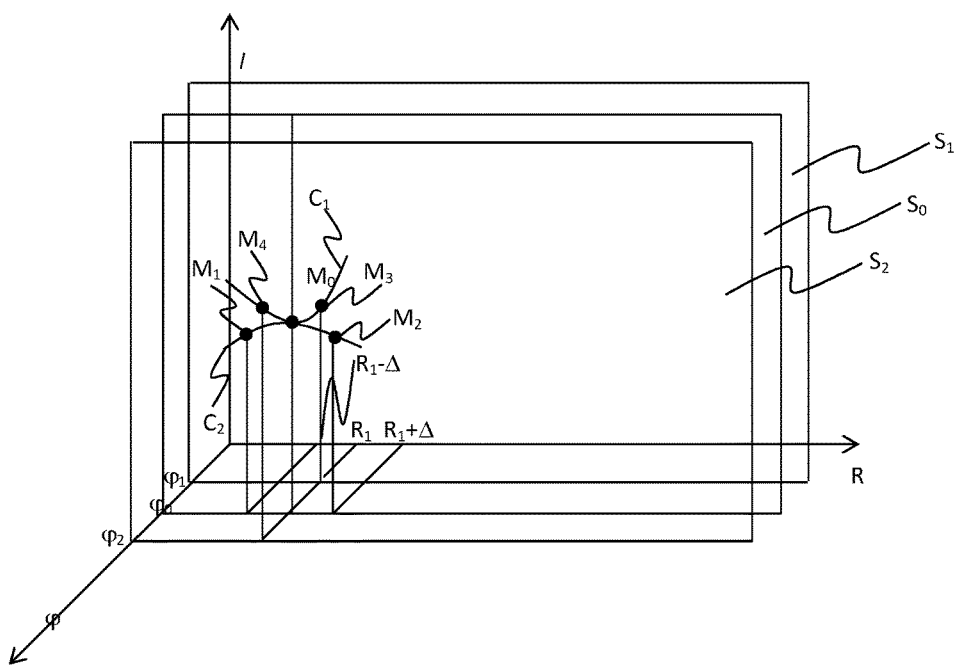

Reference is now made to FIG. 2e illustrating calculation of an IVAV which is attributed to point $M_0$. Planes $S_0$, $S_1$ and $S_2$ correspond to scanning along R-axis at constant values of angle $\varphi$, specifically at $\varphi 0$, $\varphi 1$ and $\varphi 2$, respectively. Similar to the previous consideration in Cartesian coordinates, curves $C_1$ and $C_2$ intersect each other in point $M_0$. Points $M_1$ and $M_2$ belong to curve C1. Points $M_3$ and $M_4$ belong to curve $C_2$. Along with this, points $M_1$ and $M_2$ lie in plane $S_0$, points $M_3$ in plane $S_1$ and $M_4$ in plane $S_2$.

Figure 3A:
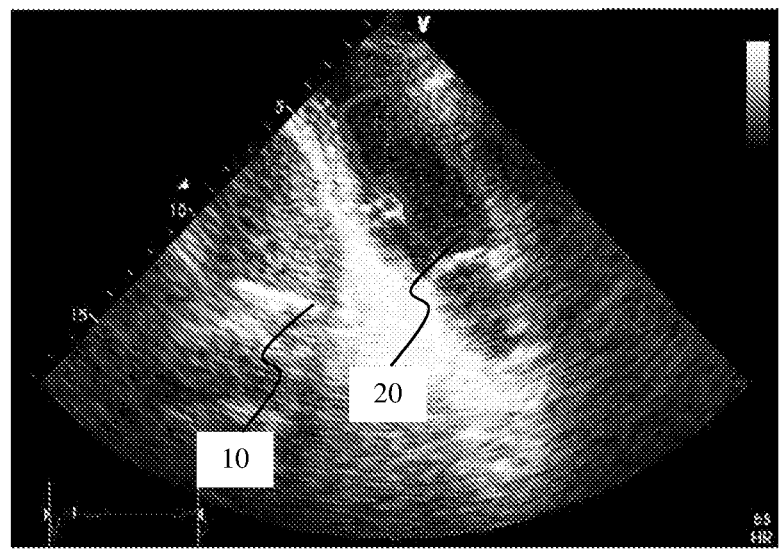
FIGS. 3a and 3b are exemplary processed echocardiographic images with closed and open edge lines, respectively.
Figure 3B:
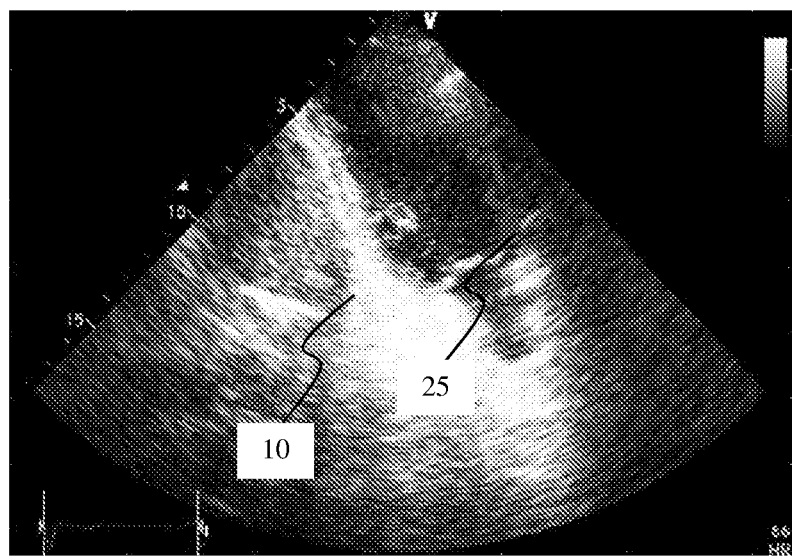

Reference is now made to FIGS. 3a and 3b, presenting exemplary processed echocardiographic images with closed and open edge lines, respectively. Referring to FIG. 2a, numeral 10 indicates an echocardiographic image. Edge line 20 borders a left ventricle of heart. Shown edge line 20 is closed.

From a practical standpoint, a median filter can be applied to the image to be processed. Additionally, polar coordinates are more convenient for the aforesaid procedure. The origin of coordinates is positioned into a central area of the ventricular cavity. This operation can be carried out automatically or manually. The center of the ventricular cavity can be found as an area of minimal intensity within the echocardiographic image.

Referring to FIG. 3b, edge line 25 is open. According to the present invention, discontinuities in the edge line should be found and closed. The discontinuities can arise in the area of an open valve.

The algorithm of forming the edge line enables calculating an area of the traced ventricular endocardium. On the basis of Simpson's formula and presumption of conicity of the left ventricle, volume of the left ventricle can be calculated from obtained locations of apical and midpoints on a 2D image. Building edge lines within 3D images is also in the scope of the present invention.

The disclosed algorithm enables building boundaries not only the left endocardium but also the right endocardium. Thus, a left ventricular wall, a right ventricular wall or pericardial sack can be evaluated. Similar, an actual wall thickness can be calculated across the whole ventricular septum, with a mean and standard deviation calculated and reported. The same can be performed for all the walls (lateral, inferior, anterior, etc.). Regions of relative thinning or thickening can be reported. Overall cardiac mass can be calculated using the difference between the total LV volume (outer, epicardial) minus the internal LV volume (endocardial).

In the case of synchronization of echocardiographic images with an EKG signal and location of the R wave, end-diastole (ED) and end-systole (ES) volumes can be obtained. In addition, ED and ES volumes can be determined by comparing different frames for maximum and minimum LV volume, respectively. The timing mark can be obtained from valve opening or closure (ED corresponds to the closed mitral valve while ES corresponds to the closed aortic valve and the open mitral valve). These volumes can then be reported (as a plot against time, for example).

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

While the technology will be described in conjunction with various embodiment(s), it will be understood that they are not intended to limit the present technology to these embodiments. On the contrary, the present technology is intended to cover alternatives, modifications and equivalents, which may be included within the spirit and scope of the various embodiments as defined by the appended claims.

Furthermore, in the following description of embodiments, numerous specific details are set forth in order to provide a thorough understanding of the present technology. However, the present technology may be practiced without these specific details. In other instances, well known methods, procedures, components, and circuits have not been described in detail as not to unnecessarily obscure aspects of the present embodiments.

Unless specifically stated otherwise as apparent from the following discussions, it is appreciated that throughout the present description of embodiments, discussions utilizing terms such as "obtaining", "calculating", "processing", "performing," "extracting," "configuring" or the like, refer to the actions and processes of a computer system, or similar electronic computing device. The computer system or similar electronic computing device manipulates and transforms data represented as physical (electronic) quantities within the computer system's registers and memories into other data similarly represented as physical quantities within the computer system memories or registers or other such information storage, transmission, or display devices, including integrated circuits down to and including chip level firmware, assembler, and hardware based micro code.

As will be explained in further detail below, the technology described herein relates to generating, storing and using semantic networks and databases to correlate physiological and psychological states of users and/or groups of users using their voice intonation data analysis.

While the invention is susceptible to various modifications and alternative forms, specific embodiments thereof have been shown by way of example in the drawings and the above detailed description. It should be understood, however, that it is not intended to limit the invention to the particular forms disclosed, but on the contrary, the intention is to cover all modifications, equivalents, and alternatives falling within the spirit and scope of the invention as defined by the appended claims.

In some embodiments, the illustrated system elements could be combined into a single hardware device or separated into multiple hardware devices. If multiple hardware devices are used, the hardware devices could be physically located proximate to or remotely from each other.

The methods can be implemented in a computer program product accessible from a computer-usable or computer-readable storage medium that provides program code for use by or in connection with a computer or any instruction execution system. A computer-usable or computer-readable storage medium can be any apparatus that can contain or store the program for use by or in connection with the computer or instruction execution system, apparatus, or device.

A data processing system suitable for storing and/or executing the corresponding program code can include at least one processor coupled directly or indirectly to computerized data storage devices such as memory elements. Input/output (I/O) devices (including but not limited to keyboards, displays, pointing devices, etc.) can be coupled to the system. Network adapters may also be coupled to the system to enable the data processing system to become coupled to other data processing systems or remote printers or storage devices through intervening private or public networks. To provide for interaction with a user, the features can be implemented on a computer with a display device, such as an LCD (liquid crystal display), virtual display, or another type of monitor for displaying information to the user, and a keyboard and an input device, such as a mouse or trackball by which the user can provide input to the computer. A computer program can be a set of instructions that can be used, directly or indirectly, in a computer. The systems and methods described herein can be implemented using programming languages such as Flash™, JAVA™, C++, C, C#, Visual Basic™, JavaScript™, PHP, XML, HTML, etc., or a combination of programming languages, including compiled or interpreted languages, and can be deployed in any form, including as a stand-alone program or as a module, component, subroutine, or other unit suitable for use in a computing environment. The software can include, but is not limited to, firmware, resident software, microcode, etc. Protocols such as SOAP/HTTP may be used in implementing interfaces between programming modules. The components and functionality described herein may be implemented on any desktop operating system executing in a virtualized or non-virtualized environment, using any programming language suitable for software development, including, but not limited to, different versions of Microsoft Windows™, Apple™ Mac™, iOS™, Android™, Unix™/X-Windows™, Linux™, etc. The system could be implemented using a web application framework, such as Ruby on Rails.

The processing system can be in communication with a computerized data storage system. The data storage system can include a non-relational or relational data store, such as a MySQL™ or other relational database. Other physical and logical database types could be used. The data store may be a database server, such as Microsoft SQL Server™, Oracle™, IBM DB2™, SQLITE™, or any other database software, relational or otherwise. The data store may store the information identifying syntactical tags and any information required to operate on syntactical tags. In some embodiments, the processing system may use object-oriented programming and may store data in objects. In these embodiments, the processing system may use an object-relational mapper (ORM) to store the data objects in a relational database. The systems and methods described herein can be implemented using any number of physical data models. In one example embodiment, an RDBMS can be used. In those embodiments, tables in the RDBMS can include columns that represent coordinates. In the case of environment tracking systems, data representing user events, virtual elements, etc. can be stored in tables in the RDBMS. The tables can have pre-defined relationships between them. The tables can also have adjuncts associated with the coordinates.

Suitable processors for the execution of a program of instructions include, but are not limited to, general and special purpose microprocessors, and the sole processor or one of multiple processors or cores, of any kind of computer. A processor may receive and store instructions and data from a computerized data storage device such as a read-only memory, a random access memory, both, or any combination of the data storage devices described herein. A processor may include any processing circuitry or control circuitry operative to control the operations and performance of an electronic device.

The processor may also include, or be operatively coupled to communicate with, one or more data storage devices for storing data. Such data storage devices can include, as non-limiting examples, magnetic disks (including internal hard disks and removable disks), magneto-optical disks, optical disks, read-only memory, random access memory, and/or flash storage. Storage devices suitable for tangibly embodying computer program instructions and data can also include all forms of non-volatile memory, including, for example, semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

The systems, modules, and methods described herein can be implemented using any combination of software or hardware elements. The systems, modules, and methods described herein can be implemented using one or more virtual machines operating alone or in combination with each other. Any applicable virtualization solution can be used for encapsulating a physical computing machine platform into a virtual machine that is executed under the control of virtualization software running on a hardware computing platform or host. The virtual machine can have both virtual system hardware and guest operating system software.

The systems and methods described herein can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks that form the Internet.

One or more embodiments of the invention may be practiced with other computer system configurations, including hand-held devices, microprocessor systems, microprocessor-based or programmable consumer electronics, minicomputers, mainframe computers, etc. The invention may also be practiced in distributed computing environments where tasks are performed by remote processing devices that are linked through a network.

The invention claimed is:

1. A method of analyzing and assessing an image, said method comprising steps of:
   a. obtaining said image in a electronic or digital form;
   b. processing said image; and
   c. establishing at least one edge line within said image;
   wherein said step of processing said image comprises:
      a. building a 3D graph of intensity distribution within said image;
      b. calculating identifying vector angle values (IVAVs); each angle adjoins to a point of said 3D intensity distribution graph which corresponds to an individual pixel of said image; said angle lies in a plane defined by an intensity axis of said image and are formed by lines being tangent to said 3D graph of intensity distribution located at nearest neighbor pixels to said individual pixel;
      c. setting a range of lower and upper thresh-hold level values (THLV1 and THLV2) between which edge points are indicatable; and
      d. indicating edge points according to said THLV1 and THLV2.

2. The method of claim 1, wherein at least one of the following is true:
   a. said image is a medical image usable for diagnostics;
   b. said step of tracing said edge line comprises a sub-step of finding discontinuities indicated by a jump of said IVAV and removing found discontinuities by connecting the previously found fragments of said edge line adjacent to said discontinuities.

3. The method of claim 2, wherein said step of processing said image comprises a sub-step of locating a central area of interest automatically or manually.

4. The method of claim 3, wherein said step of tracing said edge line is performed in polar coordinates with an origin positioned in said central area of ventricular cavity.

5. The method of claim 2, wherein said step of tracing said edge line comprises a sub-step for forming borders of an object, the object selected in the heart from a group consisting of epicardium, left ventricular endocardium, right epicardium any combination thereof.

6. The method of claim 2 comprising a step of calculating of a characteristic such as a minimal wall thickness, an epicardial ventricular volume, an endocardial ventricular volume, difference therebetween, and any combination thereof.

7. The method according to claim 1, wherein said image is an image obtained from a vehicle camera usable for identification of surrounding obstacles.

8. A device for analyzing and assessing an image; said device comprising:
   a. a unit configured for electronic or digital input of said image;
   b. a processor configured for analyzing and assessing said image;
   c. an interface unit configured for controlling said device and displaying processed images and contiguous data;
   wherein said processor is further configured for:
      a. building a 3D graph of intensity distribution within said image;
      b. calculating identifying vector angle values (IVAVs); each angle adjoins to a point of said 3D intensity distribution graph which corresponds to an individual pixel of said image; said angle lies in a plane defined by an intensity axis of said image and are formed by lines being tangent to said 3D graph of intensity distribution located at nearest neighbor pixels to said individual pixel;
      c. setting a range of lower and upper thresh-hold level values (THLV1 and THLV2) between which edge points are indicatable; and
      d. tracing said edge points according to said THLV1 and THLV2.

9. The device of claim 8, wherein at least one of the following is true:
   a. said image is a medical image usable for diagnostics; and
   b. said processor is configured for finding discontinuities indicated by a jump of said IVAV and removing found discontinuities by connecting the previously found fragments of said edge line adjacent to said discontinuities.

10. The device of claim 9, wherein said processor is configured for finding a central area of interest carried out automatically or manually.

11. The device of claim 9, wherein said processor is configured for tracing said edge line in polar coordinates with an origin positioned in said central area of interest.

12. The device of claim 9, wherein said processor is configured for forming borders of an object selected from the group consisting of: epicardium, left ventricular endocardium, right epicardium any combination thereof.

13. The device of claim 9, wherein said processor is configured for calculating of a characteristic selected from the group consisting of: a minimal wall thickness, an epicardial-ventricular volume, an endocardial ventricular volume, difference therebetween, and any combination thereof.

14. The device of claim 9, wherein said image is a medical image usable for diagnostics.

15. A non-transitory computer-readable medium having thereon software instructions configured to cause a processor to perform operations comprising:
 a. obtaining said image in an electronic or digital form;
 b. establishing at least one edge line within said image;
wherein said operation of processing said image comprises:
  a. building a 3D graph of intensity distribution within said image;
  b. calculating identifying vector angle values (IVAVs); each angle adjoins to a point of said 3D intensity distribution graph which corresponds to an individual pixel of said image; said angle lies in a plane defined by an intensity axis of said image and are formed by lines being tangent to said 3D graph of intensity distribution located at nearest neighbor pixels to said individual pixel;
  c. setting a range of lower and upper thresh-hold level values (THLV1 and THLV2) between which edge points are indicatable; and
  d. tracing said edge points according to said THLV1 and THLV2.

16. The non-transitory computer-readable medium of claim 15, wherein at least one of the following is true:
 a. said image is a medical image usable for diagnostics;
 b. the stored software instructions is configured to cause a processor to perform said step of tracing said edge line comprising a sub-step of finding discontinuities indicated by a jump of said IVAV and removing found discontinuities by connecting the previously found fragments of said edge line adjacent to said discontinuities.

17. The non-transitory computer-readable medium of claim 16, wherein the stored software instructions is configured to cause a processor to perform said step of processing said image comprising a sub-step of finding a central area of ventricular cavity carried out automatically or manually.

18. The non-transitory computer-readable medium of claim 17, wherein the stored software instructions is configured to cause a processor to perform said step of tracing said edge line in polar coordinates with an origin positioned in said central area of ventricular cavity.

19. The non-transitory computer-readable medium of claim 16, wherein the stored software instructions is configured to cause a processor to perform said step of tracing said edge line comprising a sub-step for forming borders of an object selected from the group consisting of; epicardium, left ventricular endocardium, right epicardium any combination thereof.

20. The non-transitory computer-readable medium of claim 16, wherein the stored software instructions is configured to cause a processor to perform a step of calculating of a characteristic such as thickness area or volume in the heart selected from the group consisting of a minimal wall thickness, an epicardial ventricular volume, an endocardial ventricular volume, difference therebetween, and any combination thereof.

* * * * *